US012059398B2

United States Patent
Woo et al.

(10) Patent No.: US 12,059,398 B2
(45) Date of Patent: Aug. 13, 2024

(54) COMPOSITIONS OF 1,3-BUTANEDIOL AND BETA-HYDROXYBUTYRIC ACID TO PROVIDE OPTIMAL THERAPEUTIC KETOSIS

(71) Applicant: Health Via Modern Nutrition Inc., San Francisco, CA (US)

(72) Inventors: Geoffrey Hubert Woo, San Francisco, CA (US); Christine Ensley, San Francisco, CA (US); Latt Shahril Mansor, San Francisco, CA (US)

(73) Assignee: Health Via Modern Nutrition Inc., San Francisco, CA (US)

( * ) Notice: Subject to any disclaimer, the term of this patent is extended or adjusted under 35 U.S.C. 154(b) by 16 days.

(21) Appl. No.: 17/822,727

(22) Filed: Aug. 26, 2022

(65) Prior Publication Data

US 2024/0065991 A1    Feb. 29, 2024

(51) Int. Cl.
| | | |
|---|---|---|
| A61K 31/19 | (2006.01) | |
| A23G 1/42 | (2006.01) | |
| A23L 2/02 | (2006.01) | |
| A23L 2/52 | (2006.01) | |
| A23L 33/10 | (2016.01) | |
| A61K 9/00 | (2006.01) | |
| A61K 31/047 | (2006.01) | |

(52) U.S. Cl.
CPC ............. *A61K 31/19* (2013.01); *A23G 1/42* (2013.01); *A23L 2/02* (2013.01); *A23L 2/52* (2013.01); *A23L 33/10* (2016.08); *A61K 9/0056* (2013.01); *A61K 9/0095* (2013.01); *A61K 31/047* (2013.01); *A23V 2002/00* (2013.01)

(58) Field of Classification Search
CPC .... A61K 31/19; A61K 9/0056; A61K 9/0095; A61K 31/047; A23L 33/10; A23L 2/02; A23L 2/52; A23G 1/42; A23V 2002/00
See application file for complete search history.

(56) References Cited

U.S. PATENT DOCUMENTS

| | | |
|---|---|---|
| 8,642,654 B2 | 2/2014 | Clarke |
| 11,044,932 B1 | 6/2021 | Price |
| 11,141,392 B2 | 10/2021 | Price |
| 2017/0296501 A1 | 10/2017 | Lowery et al. |
| 2018/0057846 A1 | 3/2018 | Llosa et al. |
| 2019/0177673 A1 | 6/2019 | Llosa |
| 2019/0248730 A1* | 8/2019 | Verdin ............... A61P 13/12 |
| 2020/0129463 A1 | 4/2020 | Lowery et al. |
| 2020/0268701 A1 | 8/2020 | D'Agostino |
| 2020/0289444 A1* | 9/2020 | Thomas ............ A61K 31/047 |
| 2020/0397792 A1 | 12/2020 | Millet |
| 2021/0205241 A1 | 7/2021 | Millet |
| 2021/0322349 A1 | 10/2021 | Price |
| 2022/0095664 A1* | 3/2022 | Price ...................... A23L 33/40 |
| 2022/0133673 A1 | 5/2022 | Millet |

FOREIGN PATENT DOCUMENTS

| | | |
|---|---|---|
| FR | 3062303 | 8/2018 |
| WO | 2015199142 | 12/2015 |
| WO | 2020167690 | 8/2020 |
| WO | 2022046396 | 3/2022 |

OTHER PUBLICATIONS

McCarthy et al. J Pharmacol Exp Ther. Dec. 2021; 379(3): 245-252. Published online Dec. 2021. (Year: 2021).*
McCarthy CG, Waigi EW, Yeoh BS, Mell B, Vijay-Kumar M, Wenceslau CF, Joe B. Low-dose 1,3-butanediol reverses age-associated vascular dysfunction independent of ketone body β-hydroxybutyrate. Am J Physiol Heart Circ Physiol. Mar. 1, 2022;322(3):H466-H473. doi: 10.1152/ajpheart.00486.2021. Epub Feb. 11, 2022. PMID: 35148235; PMCID: PMC8897007.
McCarthy DG, Bostad W, Powley FJ, Little JP, Richards DL, Gibala MJ. Increased cardiorespiratory stress during submaximal cycling after ketone monoester ingestion in endurance-trained adults. Appl Physiol Nutr Metab. Aug. 2021;46(8):986-993. doi: 10.1139/apnm-2020-0999. Epub Mar. 1, 2021. PMID: 33646860.
Stubbs BJ, Cox PJ, Evans RD, Santer P, Miller JJ, Faull OK, Magor-Elliott S, Hiyama S, Stirling M, Clarke K. On the Metabolism of Exogenous Ketones in Humans. Front Physiol. Oct. 30, 2017;8:848. doi: 10.3389/fphys.2017.00848. PMID: 29163194; PMCID: PMC5670148.
Stefan M, Sharp M, Gheith R, Lowery R, Wilson J. The Effect of Exogenous Beta-Hydroxybutyrate Salt Supplementation on Metrics of Safety and Health in Adolescents. Nutrients. Mar. 5, 2021;13(3):854. doi: 10.3390/nu13030854. PMID: 33807731; PMCID: PMC8000900.

(Continued)

*Primary Examiner* — Jeffrey S Lundgren
*Assistant Examiner* — William Y Lee
(74) *Attorney, Agent, or Firm* — David R. Conklin; Kirton McConkie

(57) ABSTRACT

Nutritional compositions contain a mixture of ketogenic ingredients including from 80 to 99% weight % 1,3-butanediol (BDO), preferably R-1,3-butanediol, and from 1 to 20 weight % beta-hydroxybutyric acid (BHB), preferably D-beta-hydroxybutyric acid, or an equivalent molar amount of its conjugate base beta-hydroxybutyrate, salts, monoesters, polyesters, or mixtures thereof. In some embodiments, the nutritional compositions for providing ketosis are prepared for oral administration in a solid form, such as bars, bites, tablets, pills or capsules, in a liquid form, such as smoothies, goos, water, carbonated beverages, soft drinks, fermented beverage suspensions, solutions and emulsions, or in a powder form that can be used to prepare drink mixes or can be added as a supplement to other food or drink products. Methods of providing ketosis in a subject include delivering optimal therapeutic ketosis, with rapidity into and extended duration of blood concentrations of D-BHB of between 1 mM and 2.5 mM.

16 Claims, 3 Drawing Sheets

(56) References Cited

OTHER PUBLICATIONS

Nielsen R, Møller N, Gormsen LC, Tolbod LP, Hansson NH, Sorensen J, Harms HJ, Frøkiær J, Eiskjaer H, Jespersen NR, Mellemkjaer S, Lassen TR, Pryds K, Bøtker HE, Wiggers H. Cardiovascular Effects of Treatment With the Ketone Body 3-Hydroxybutyrate in Chronic Heart Failure Patients. Circulation. Apr. 30, 2019;139(18):2129-2141. doi: 10.1161/CIRCULATIONAHA. 118.036459. PMID: 30884964; PMCID: PMC6493702.

Mansor LS, Woo GH. Ketones for Post-exercise Recovery: Potential Applications and Mechanisms. Front Physiol. Jan. 26, 2021;11:613648. doi: 10.3389/fphys.2020.613648. PMID: 33574765; PMCID: PMC7870714.

Dearlove DJ, Harrison OK, Hodson L, Jefferson A, Clarke K, Cox PJ. The Effect of Blood Ketone Concentration and Exercise Intensity on Exogenous Ketone Oxidation Rates in Athletes. Med Sci Sports Exerc. Mar. 1, 2021;53(3):505-516. doi: 10.1249/MSS. 0000000000002502. PMID: 32868580; PMCID: PMC7886359.

Clark D, Munten S, Herzig KH, Gagnon DD. Exogenous Ketone Salt Supplementation and Whole-Body Cooling Do Not Improve Short-Term Physical Performance. Front Nutr. Jul. 15, 2021;8:663206. doi: 10.3389/fnut.2021.663206. PMID: 34336907; PMCID: PMC8319384.

Falkenhain, et al. The Effect of Novel Exogenous Ketone Supplements on Blood Beta-Hydroxybutyrate and Glucose. Aug. 12, 2022 [retrieved Nov. 13, 2023] Retrieved from Intrnet URL: https://www.mexrxiv.org/content/10.1101/2022.08.11.22278668v1.

* cited by examiner

COMPOSITIONS OF 1,3-BUTANEDIOL AND BETA-HYDROXYBUTYRIC ACID TO PROVIDE OPTIMAL THERAPEUTIC KETOSIS

FIELD OF THE INVENTION

The present invention relates to compositions and methods for delivering "optimal therapeutic ketosis", and accounts for improved speed of entering "optimal therapeutic ketosis" D-beta-hydroxybutyric acid (D-BHB) blood concentration, improved duration of time within the "optimal therapeutic ketosis" D-BHB blood concentration, mitigating risk of crossing above the high-end bound of "optimal therapeutic ketosis", and improving palatability and GI distress risk inherent with prior art ketone and ketogenic precursor compositions.

The invention relates to compositions comprising therapeutically effective amounts of 1,3-butanediol (BDO), present as R-1,3-butanediol, S-1,3-butanediol, or racemic 1,3-butanediol, in combination with therapeutically effective active amounts of beta-hydroxybutyric acid (BHB), present as D-beta-hydroxybutyric acid (D-BHB), L-beta-hydroxybutyric acid (L-BHB), racemic beta-hydroxybutyric acid and/or its conjugate base beta-hydroxybutyrate present as D-beta-hydroxybutyrate, L-beta-hydroxybutyrate, racemic beta-hydroxybutyrate or salts, monoesters, or polyesters thereof. The disclosed compositions may comprise equivalent molar mixtures of BHB, beta-hydroxybutyrate, and its salts and esters thereof. R-1,3-butanediol and D-beta-hydroxybutyric acid are presently preferred. The compositions provide "optimal therapeutic ketosis" by producing, and simultaneously account for improved speed of entering, "optimal therapeutic ketosis" D-BHB blood concentration, improved duration of time within the "optimal therapeutic ketosis" D-BHB blood concentration, mitigating risk of crossing above the high-end bound of "optimal therapeutic ketosis", and improving palatability and GI distress risk inherent with the prior art ketone and ketogenic precursor compositions.

BACKGROUND OF THE INVENTION

The present disclosure relates to compositions and methods for providing "optimal therapeutic ketosis". Ketosis is a metabolic state characterized by raised levels of ketone bodies in the body tissues. One physiologically significant ketone body is D-beta-hydroxybutyrate (D-BHB) and physiological markers for ketosis is determined by the blood concentration of D-BHB. Ketosis is typically defined by blood concentrations of D-BHB over 0.5 mM.

Ketosis may be pathological due to a condition such as diabetes. Ketosis may be the consequence of diet that is very low in carbohydrates, fasting, or starvation. Ketosis may result from extreme exercise. Ketosis may be induced by ingestion of exogenous ketone bodies, including ketogenic precursors.

The body naturally converts fat to ketone bodies during fat metabolism. Ketone bodies may provide a source of energy for both peripheral tissues and the central nervous system, particularly under carbohydrate deprivation. Ketone bodies are the most energy-efficient fuel and yield more ATP per mole of substrate than pyruvate.

A number of researchers, including Price et al, Clarke et al, Llosa et al, and Millet et al, teach ketone and ketogenic precursor compositions that deliver BHB. While ingestion of these ketogenic precursor compositions, may produce ketosis as defined by delivering blood concentrations of D-BHB over 0.5 mM, they do not anticipate or contemplate a number of scenarios relating to the under-delivery of physiologically relevant doses of BHB and the over-delivery of a concentration of D-BHB that is counter-productive and detrimental to a number of physiological, metabolic and palatability markers. They also do not anticipate or contemplate the consequences associated with the speed of entering ketosis and the duration of ketosis. Many ketogenic precursor compositions induce a rapid spike and crash of D-BHB levels in the blood, which exacerbates common negative side effects including nausea and GI distress. Specifically, when blood BHB is too high, there is a significant drop in blood pH and increase in cardiorespiratory stress biomarkers (McCarthy D G, Bostad W, Powley F J, Little J P, Richards D L, Gibala M J. Increased cardiorespiratory stress during submaximal cycling after ketone monoester ingestion in endurance-trained adults. Appl Physiol Nutr Metab. 2021 August; 46(8):986-993. doi: 10.1139/apnm-2020-0999. Epub 2021 Mar. 1. PMID: 33646860) and risk of GI issues. BHB oxidation and performance increase is most noticeable at ~2 mM while increasing beyond that point has little to no increase in BHB oxidation (Dearlove D J, Harrison O K, Hodson L, Jefferson A, Clarke K, Cox P J., The Effect of Blood Ketone Concentration and Exercise Intensity on Exogenous Ketone Oxidation Rates in Athletes., Med Sci Sports Exerc., 2021 Mar. 1; 53(3):505-516. doi: 10.1249/MSS.0000000000002502. PMID: 32868580; PMCID: PMC7886359).

As used herein, an "optimal therapeutic ketosis" is defined by D-BHB blood concentrations of between 1 to 2.5 mM D-BHB, as defined by the authors in Mansor and Woo, Ketones for Post-exercise Recovery: Potential Applications and Mechanisms, https://www.frontiersin.org/articles/10.3389/fphys0.2020.613648/full. Neilsen et al. (https://www.ncbi.nlm.nih.gov/pmc/articles/PMC6493702/) further supports the low end (1 mM D-BHB). The high end (2.5 mM D-BHB) is further validated by (Dearlove D J, Harrison O K, Hodson L, Jefferson A, Clarke K, Cox P J., The Effect of Blood Ketone Concentration and Exercise Intensity on Exogenous Ketone Oxidation Rates in Athletes, Med. Sci. Sports Exerc., 2021 Mar. 1; 53(3):505-516. doi: 10.1249/MSS 0.0000000000002502. PMID: 32868580; PMCID: PMC7886359).

The prior art also fails to contemplate nor distinguish the salubrious physiological benefit of BDO, independent of its role in BHB biosynthesis, especially as it relates to vasodilation and nitric oxide synthase (McCarthy C G, et al. haps://journals.physiology.org/doi/abs/10.1152/ajpheart.00486.2021?journalCode=ajpheart).

It would be an advancement in the art to provide novel and synergistic compositions and methods that simultaneously address one or more of: the speed of entering "optimal therapeutic ketosis" D-BHB blood concentration; the duration of time within the "optimal therapeutic ketosis" D-BHB blood concentration; mitigating the risk of crossing above the high-end bound of "optimal therapeutic ketosis"; and improving palatability and GI distress risk common with the prior art of ketone and ketogenic precursor compositions

BRIEF SUMMARY OF THE INVENTION

The present disclosure relates generally to nutritional compositions and methods for providing therapeutic ketosis. As used herein, a desired or target therapeutic ketosis level, referred to as "optimal therapeutic ketosis," is defined as a blood D-BHB level between 1 to 2.5 mM D-BHB.

Disclosed nutritional compositions include a mixture of ketogenic ingredients. The ketogenic ingredients include 1,3-butanediol (BDO) selected from R-1,3-butanediol, S-1,3-butanediol, and racemic 1,3-butanediol, with R-1,3-butandediol being presently preferred. In one non-limiting embodiment, the ketogenic ingredients further include beta-hydroxybutyric acid (BHB) selected from D-beta-hydroxybutyric (D-BHB) acid, L-beta-hydroxybutyric (L-BHB) acid, racemic beta-hydroxybutyric acid and/or an equivalent molar amount of its conjugate base beta-hydroxybutyrate selected from D-beta-hydroxybutyrate, L-beta-hydroxybutyrate, racemic beta-hydroxybutyrate or a salt, monoester, polyester, or mixture thereof. D-BHB or its equivalent conjugate base, salt or ester is presently preferred.

Salts of beta-hydroxybutyrate include mineral and organic salts. Non-limiting examples of mineral salts include sodium, potassium, magnesium, and calcium salts of BHB. Non-limiting examples of organic salts include formates, acetates, butyrates, carboxylates, tartrates, malates, citrates, gluconates, maleates, lactates, glycerates, phosphonates, organophosphates, glycinates, arginine, lysine, histidine, ornithine, creatine, agmatine, and citrulline salts of BHB. Combinations of different salts may be used.

The ketogenic ingredients of the disclosed nutritional compositions contain from 80 to 99% by weight of BDO and from 1 to 20% by weight of D-BHB. As used herein, reference to a specific amount of "D-BHB," such as "1 to 20% by weight of D-BHB" includes equivalent molar mixtures of D-BHB and its conjugate base, salt, or ester thereof. As used herein, reference to a specific amount of "BHB," such as "1 to 20% by weight of BHB" includes equivalent molar mixtures of BHB and its conjugate base, salt, or ester thereof.

In a non-limiting embodiment of the disclosed nutritional compositions, the ketogenic ingredients of the disclosed nutritional compositions contain from 85 to 99% by weight of BDO and from 1 to 15% by weight of D-BHB.

In a non-limiting embodiment of the disclosed nutritional compositions, the ketogenic ingredients contain from 85 to 95% by weight BDO and from 15 to 5% by weight of D-BHB.

In a non-limiting embodiment of the disclosed nutritional compositions, the ketogenic ingredients contain from 85 to 92% by weight BDO and from 15 to 8% by weight of D-BHB.

In a non-limiting embodiment of the disclosed nutritional compositions, the ketogenic ingredients contain from 87 to 90% by weight BDO and from 13 to 10% by weight of D-BHB.

In a non-limiting embodiment of the disclosed nutritional compositions, the ketogenic ingredients are present in an amount ranging from 1 gram to 100 grams.

In a non-limiting embodiment of the disclosed nutritional compositions, the ketogenic ingredients are present in an amount ranging from 5 gram to 50 grams.

In a non-limiting embodiment of the disclosed nutritional compositions, the ketogenic ingredients are present in an amount ranging from 10 gram to 30 grams.

1,3-butanediol (BDO) has the formula $HOCH_2CH_2CH(OH)CH_3$. It is a chiral diol. As used herein, "1,3-butanediol" includes R-1,3-butanediol, S-1,3-butanediol, or racemic 1,3-butanediol. R-1,3-butanediol is presently preferred.

Beta-hOroxybutyric (BHB) acid has the formula $CH_3CH(OH)CH_2CO_2H$. It is a chiral compound with two enantiomers: D-beta-hydroxybutyric acid and L-beta-hydroxybutyric acid. In humans, D-beta-hydroxybutyrate is synthesized in the liver via the metabolism of fatty acids (e.g., butyrate). As used herein, "beta-hydroxybutyric acid" includes D-beta-hydroxybutyric acid, L-beta-hydroxybutyric acid or racemic beta-hydroxy bu c acid. The "D" enantiomer form is presently preferred.

The disclosed invention includes one or more methods of providing therapeutic ketosis. The disclosed methods include administering to the subject any one of the disclosed nutritional compositions containing a therapeutically effective amount of 1,3-butanediol, in the form of R-1,3-butanediol, S-1,3-butanediol, or racemic 1,3-butanediol (preferably R-1,3-butanediol) and a therapeutically effective amount of beta-hydroxybutyric (BHB) acid, in the form of D-beta-hydroxybutyric (D-BHB) acid, L-beta-hydroxybutyric (L-BHB) acid, racemic beta-hydroxybutyric acid and/or an equivalent molar amount of its conjugate base beta-hydroxybutyrate, in the form of D-beta-hydroxybutyrate, L-beta-hydroxybutyrate, racemic beta-hydroxybutyrate, or a salt monoester, polyester, or mixture thereof (preferably D-BHB and its equivalents).

In one or more of the disclosed methods, a disclosed nutritional composition is administered when "optimal therapeutic ketosis" is desired.

In one or more of the disclosed methods, a disclosed nutritional composition is administered to provide optimal therapeutic ketosis in a subject as measured by a blood concentration of D-BHB in a range from 1 mM to 2.5 mM, and the method takes less than 30 minutes to achieve optimal therapeutic ketosis and zero time above the optimal therapeutic ketosis range in the subject.

The disclosed compositions may be provided in any oral consumable form. It is within the scope of the disclosed invention to configure the disclosed compositions into formulations suitable for parenteral (including subcutaneous, intradermal, intramuscular, and intravenous) and rectal administration. In some embodiments, the disclosed compositions are in the form of a tablet, capsule, or pill suitable for oral administration. In some embodiments, the disclosed compositions are in liquid formulations (e.g., water, carbonated beverages, soft drinks, fermented beverages) suitable for oral administration. In some embodiments, the disclosed compositions are in the form of powders that can be used to prepare drink mixes or can be added as a supplement to other food or drink products. One or more pharmaceutically acceptable carriers may be provided. In various embodiments, the compositions are formulated for oral administration, including immediate release, extended release, and sustained release formulations.

Various embodiments are described herein. It will be understood that the embodiments described herein may be combined not only as listed, but in other suitable combinations in accordance with the scope of the invention.

It is to be understood that both the foregoing general description and the following detailed description are examples and explanatory and are not restrictive of the invention, as claimed. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

DETAILED DESCRIPTION OF THE INVENTION

Figure 1:
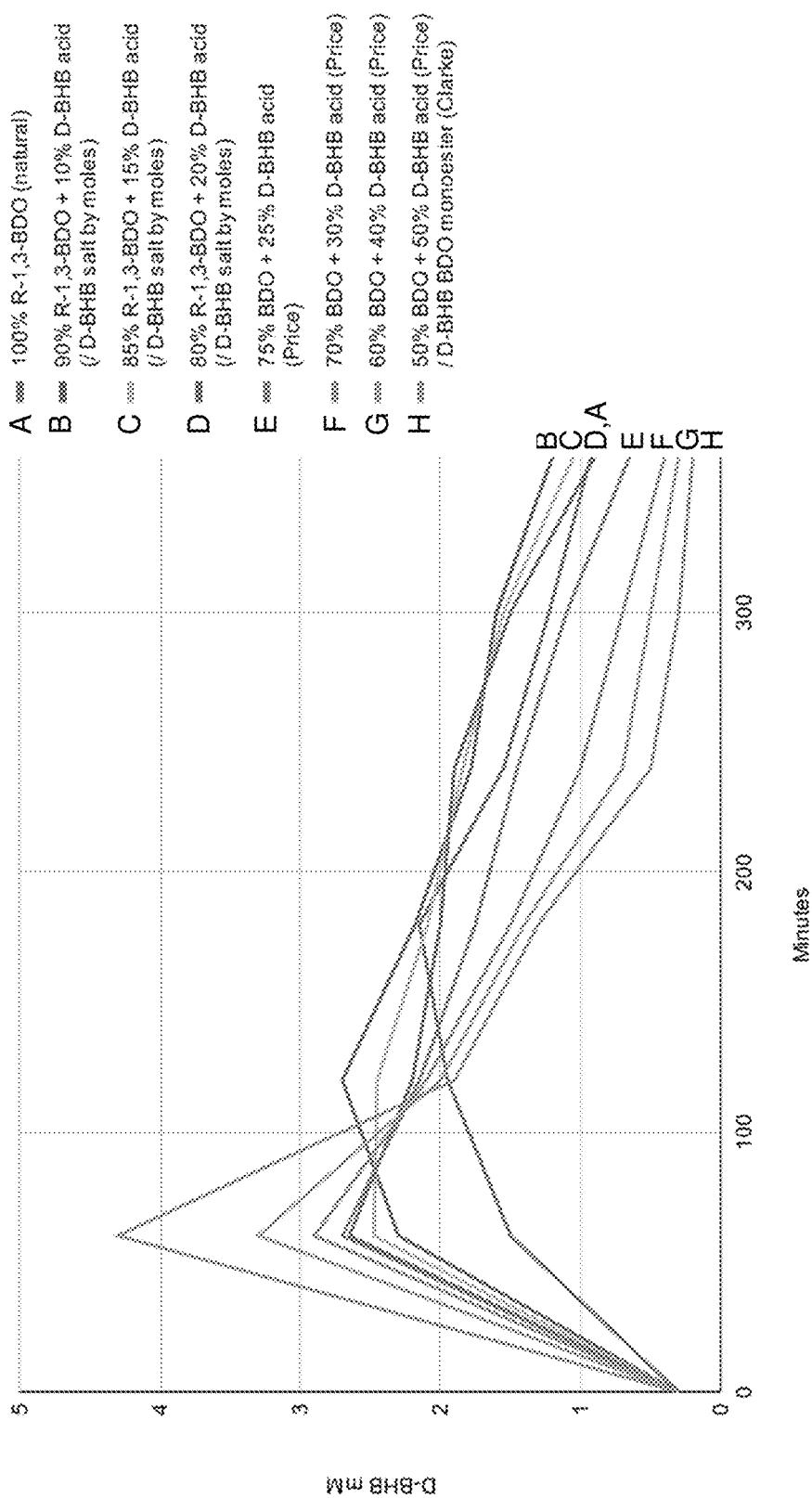
FIG. 1 is a graph showing the blood D-BHB pharmacokinetics for eight ketogenic compositions, reporting blood D-BHB mM over a time period of six hours following ingestion of the ketogenic compositions.

The present invention relates to nutritional compositions and methods for providing "optimal therapeutic ketosis". "Optimal therapeutic ketosis" is defined herein as a blood D-BHB level between 1 to 2.5 mM. The disclosed nutritional compositions provide elevated and sustained "optimal therapeutic ketosis." The disclosed nutritional compositions may improve speed of entering "optimal therapeutic ketosis" D-BHB blood concentration, improve duration of time within the "optimal therapeutic ketosis" D-BHB blood concentration, mitigate risk of crossing above the high-end bound of "optimal therapeutic ketosis", and improve palatability and GI distress risk inherent with prior art ketone and ketogenic precursor compositions.

Consensus of literature demonstrates that concentrations below 1 mM are irrelevant for acute physiological benefit (Stefan et al. The Effect of Exogenous Beta-Hydroxybutyrate Salt Supplementation on Metrics of Safety and Health in Adolescents https://www.ncbi.nlm.nih.gov/pmc/articles/PMC8000900/, Clark et al. Exogenous Ketone Salt Supplementation and Whole-Bdy Cooling Do Not Improve Short-Term Physical Performance https://www.frontiersin.org/articles/10.3389/fnut.2021.663206/full).

Recent data suggest that concentrations above 2.5 mM cause adverse impact across a number of physiological, metabolic and palatability markers. A rapid spike and crash of D-BHB levels in the blood exacerbates common negative side effects including nausea and GI distress. Specifically, when blood BHB is too high, there is a significant drop in blood pH and increase in cardiorespiratory stress biomarkers (McCarthy D G, Bostad W, Powley F J, Little J P, Richards D L, Gibala M J. Increased cardiorespiratory stress during submaximal cycling after ketone monoester ingestion in endurance-trained adults. Appl Physiol Nutr Metab. 2021 August; 46(8):986-993. doi: 10.1139/apnm-2020-0999. Epub 2021 Mar. 1. PMID: 33646860) and risk of GI issues. BHB oxidation and performance increase is most noticeable at ~2 mM while increasing beyond that point has little to no increase in BHB oxidation (Dearlove D J, Harrison O K, Hodson L, Jefferson A, Clarke K, Cox P J. The Effect of Blood Ketone Concentration and Exercise Intensity on Exogenous Ketone Oxidation Rates in Athletes. Med Sci Sports Exerc. 2021 Mar. 1; 53(3):505-516. doi: 10.1249/MSS.0000000000002502. PMID: 32868580; PMCID: PMC7886359).

An "optimal therapeutic ketosis" is defined by D-BHB blood concentrations of between 1 to 2.5 mM D-BHB, as first defined by the authors in Mansor and Woo Ketones for Post-exercise Recovery: Potential Applications and Mechanisms https://www.frontiers in.org/articles/10.3389/fphys0.2020.613648/full. Neilsen et al. (https://www.ncbi.nlm.nih.gov/pmc/articles/PMC 6493702/) further supports the low end concentration (1 mM D-BHB). The high end concentration (2.5 mM D-BHB) is further validated by (Dearlove D J, Harrison O K, Hodson L, Jefferson A, Clarke K, Cox P J. The Effect of Blood Ketone Concentration and Exercise Intensity on Exogenous Ketone Oxidation Rates in Athletes. Med Sci Sports Exerc. 2021 Mar. 1; 53(3):505-516. doi: 10.1249/MSS.0000000000002502. PMID: 32868580; PMCID: PMC7886359).

Furthermore, McCarthy C G in March 2022 (https://journals.physiology.org/doi/abs/10.1152/ajpheart.00486.2021?journalCode=ajpheart) observed that BDO was sufficient to reverse age-associated endothelial-dependent and -independent dysfunction, and this was not associated with increased blood BHB concentration. Further analysis of the direct vasodilator mechanisms of 1,3-BDO revealed that it is predominantly an endothelium-dependent vasodilator through activation of potassium channels and nitric oxide synthase. Therefore, there is a specific and not previously contemplated benefit of BDO as a primary component of the disclosed nutritional compositions, whereas in the prior art, BDO is only contemplated as a ketogenic precursor to BHB.

The terminology used herein is for the purpose of describing particular embodiments only and is not intended to be limiting. In this specification and in the claims that follow, reference will be made to a number of terms, which shall be defined to have the definitions set forth herein. Unless otherwise defined, all technical and scientific terms used herein have the same meaning as commonly understood by one of ordinary skill in the art to which this invention belongs. The singular forms also include the plural unless the context clearly dictates otherwise. Thus, the singular forms "a," "an" and "the" include plural referents unless the context clearly dictates otherwise.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment. Additionally, while the following description refers to several embodiments and examples of the various components and processes of the described invention, all of the described embodiments and examples are to be considered, in all respects, as illustrative only and not as being limiting in any manner. Furthermore, the described features, structures, characteristics, processes, or methods of the invention may be combined in any suitable manner in one or more embodiments.

As used herein, the expression [A], [B], [C], "and/or" [D] means that one or more of the cases connected by the expression "and/or" may occur individually or in combination. Thus, the expression means [A] or [B] or [C] or [D] may occur individually, or combinations of any two or more cases may occur, such as [A] and [B], [A] and [C], [B] and [C], [A], [C], and [D], etc.

As used herein, unless explicitly stated otherwise or clearly implied otherwise, the term "about" refers to a range of values plus or minus 10 percent ("±10%"), e.g., about 1.0 encompasses values from 0.9 to 1.1.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4, and from 3-5, etc. This same principle applies to ranges reciting only one numerical value. Furthermore, such an interpretation should apply regardless of the range or the characteristics being described.

"Active agent" and "therapeutic agent" means a compound that exerts a positive therapeutic effect on the health and well-being of a subject. Active agent can refer not only to a single active agent but also to a combination of two or more different active agents. "Active" is further defined by distinguishing a "ketogenic portion" as compounds that directly deliver BHB or the biosynthesis of BHB, as compared to the independent salubrious benefit of BDO, distinct from its role in the biosynthesis of BHB.

As used herein, the term "beverage" can relate to consumable liquids including but not limited to water, carbonated water, naturally and/or artificially flavored waters, soft drinks, teas, juices, milk, extractions, fermented beverages, alcohol-containing beverages, and other known consumable liquids. In some embodiments, the beverage is provided in a single-dose container for consumer use. Alternatively, the beverage is provided in a multi-dose container.

"Sustained release" and "extended release" means an active agent formulation that provides for gradual release of an active agent over an extended period of time, and typically, although not necessarily, results in substantially constant blood levels of an active agent over an extended time period.

"Dosage form" means any form of a composition for administration to a subject (typically a human seeking a therapeutic or synergistic effect). "Dose" refers to an amount of active agent. A single tablet or capsule is a unit dosage form. Multiple unit dosage forms can be administered to provide a therapeutically effective dose. A dosage form can include a combination of dosage forms.

"Therapeutically effective amount" refers to a nontoxic but sufficient amount of an active agent to achieve a desired therapeutic effect.

The term "composition" refers to a composition that is suitable for administration to a subject. In general, a "composition" is sterile, and preferably free of contaminants that are capable of eliciting an undesirable response within the subject.

The term "flavoring agent" means the essential oil, oleoresin, essence or extractive, protein hydrolysate, distillate, or any product of roasting, heating or enzymolysis, which contains the flavoring constituents derived from a spice, fruit or fruit juice, vegetable or vegetable juice, edible yeast, herb, bark, bud, root, leaf or similar plant material, meat, seafood, poultry, eggs, dairy products, or fermentation products thereof, whose significant function in food is flavoring rather than nutritional.

Percentages and ratios used herein, unless otherwise indicated, are by weight.

Certain nutritional compositions of the disclosed invention comprise a therapeutically effective amount of R-1,3-butanediol, S-1,3-butanediol, or racemic 1,3-butanediol (preferably R-1,3-butanediol) in combination with a therapeutically effective amount of one or more additional active ingredients selected from D-beta-hydroxybutyric (D-BHB) acid, L-beta-hydroxybutyric (L-BHB) acid, racemic beta-hydroxybutyric acid or D-beta-hydroxybutyrate, L-beta-hydroxybutyrate, racemic beta-hydroxybutyrate, a monoester, polyester, organic or inorganic salt, or mixtures thereof (preferably D-BHB).

The compositions may also comprise one or more pharmaceutically acceptable (approved by a state or federal regulatory agency for use in humans, or is listed in the U.S. Pharmacopia, the European Pharmacopia) excipients or carriers. The terms "excipient" or "carrier" as used herein broadly refers to a biologically inactive substance used in combination with the active agents of the formulation. An excipient can be used, for example, as a solubilizing agent, a stabilizing agent, a diluent, an inert carrier, a preservative, a binder, a disintegrant, a coating agent, a flavoring agent, or a coloring agent. Preferably, at least one excipient is chosen to provide one or more beneficial physical properties to the formulation, such as increased stability and/or solubility to the therapeutic agents.

Non-limiting examples of suitable excipients for liquid or beverage formulations include flavoring agents, sweeteners, including nutritive and non-nutritive sweeteners, acidifiers such as citric, malic acid, tartaric acid, and phosphoric acid, and emulsifiers such as hydrocolloids like xanthan, gum acacia and gum acacia, modified starches, pectin, carrageenan, casein, and inulin. Non-limiting examples of sweeteners include *stevia*, steviol glycosides, allulose, monk fruit, and mogrosides. Non-limiting examples of suitable excipients for solid formulations include flow agents such as silicon dioxide, magnesium stearate, and stearic acid, binders such as guar gum, xanthan gum, and acacia gum, carriers such as naturally occurring complex carbohydrates, acidifiers such as naturally-occurring acids including citric acid, malic acid, tartaric acid, and aspartic acid.

Solutions and suspensions used for the delivery can include the following components: a sterile diluent such as water, saline solution, fixed oils, polyethylene glycols, glycerine, polylene glycol, polysorbate, tocopherol polyethylene glycol succinate (TPGS), or other synthetic solvents; antibacterial agents such as benzyl alcohol or methyl parabens; antioxidants such as ascorbic acid or sodium bisulfite; chelating agents such as ethylenediamineteraacetic acid; buffers such as acetates, citrates or phosphates, and agents for the adjustment of tonicity such as sodium chloride or dextrose. The pH can be adjusted with acids or bases, such as hydrochloric acid or sodium hydroxide.

In some embodiments, the nutritional compositions for providing ketosis are prepared in a solid form such as a bar, bite, powder, tablet, pill or capsule for oral administration. In alternative embodiments, liquid formulations for oral administration may take such forms as smoothies, goos, water, carbonated beverages, soft drinks, fermented beverage suspensions, solutions and emulsions, and may contain formulatory agents such as suspending, stabilizing and/or dispersing agents. In some embodiments, the disclosed compositions may be in the form of powders that can be used to prepare drink mixes or can be added as a supplement to other food or drink products.

The composition itself provides for an "optimal therapeutic ketosis" blood concentration of BHB, and may be further optimized by dosage forms, e.g., an oral dosage form, which may provide for a combination of rapid release and extended release or sustained release, from the dosage form to the subject's body over a time period in the range of about 2 to about 4 hours.

In some embodiments, it may be especially advantageous to formulate compositions of the invention in unit dosage form for ease of administration and uniformity of dosage. The term "unit dosage forms" as used herein refers to physically discrete units suited as unitary dosages for the individuals to be treated. That is, the compositions are formulated into discrete dosage units each containing a predetermined, "unit dosage" quantity of an active agent calculated to produce the desired therapeutic effect in association with the required pharmaceutical carrier. The specifications of unit dosage forms of the invention are dependent on the unique characteristics of the active agent to be delivered. Dosages can further be determined by reference to the usual dose and manner of administration of the ingredients. It should be noted that, in some cases, two or more individual dosage units in combination provide a therapeutically effective amount of the active agent, e.g., two tablets or capsules taken together may provide a therapeutically effective dosage of a first or second therapeutic agent, such that the unit dosage in each tablet or capsule is approximately 50% of the therapeutically effective amount.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like.

Capsules are another oral dosage form of the present invention, wherein the R-1,3-butanediol, S-1,3-butanediol, or racemic 1,3-butanediol (preferably R-1,3-butanediol), and the D-beta-hydroxybutyric acid (D-BHB), L-beta-hydroxybutyric acid (L-BHB), or racemic beta-hydroxybutyric acid and/or an equivalent molar amount of its conjugate base beta-hydroxybutyrate, a salt, monoester, polyester, or mixture thereof (preferably D-BHB), are encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like.

Oral dosage forms, whether tablets, capsules, caplets, or particulates, if desired, may be formulated so as to provide for extended or controlled release of the R-1,3-butanediol, S-1,3-butanediol, or racemic 1,3-butanediol (preferably R-1,3-butanediol) and the D-beta-hydroxybutyric acid (D-BHB), or L-beta-hydroxybutyric acid (L-BHB), or racemic beta-hydroxybutyric acid and/or an equivalent molar amount of its conjugate base beta-hydroxybutyrate, a salt, monoester, polyester, or mixture thereof (preferably D-BHB).

Generally, as will be appreciated by those of ordinary skill in the art, extended release and sustained release dosage forms are formulated by dispersing at least one of the two or more active therapeutic agents within a matrix of a gradually hydrolyzable material such as a hydrophilic polymer, or by coating a solid, active agent-containing dosage form with such a material. Hydrophilic polymers useful for providing an extended release or a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Other features and advantages of the present invention are apparent from the different examples that follow. The examples below illustrate different aspects and embodiments of the present invention and how to make and practice them. The examples do not limit the claimed invention. Although methods and materials similar or equivalent to those described herein can be used in the practice of the present invention, suitable methods and materials are described below. Based on the present disclosure the skilled artisan can identify and employ other components and methodology useful for practicing the present invention.

Examples 1-4: Ketogenic Nutritional Lemonade Beverages

Examples 1-4 describe a process for preparing several therapeutically effective beverages of R-1,3-butanediol and D-BHB suitable for oral administration. The ingredients are mixed in water in the amounts set forth in Table 1. Lemon juice and D-BHB are used as the pH control. Flavoring and sweetener are in the form of lemon juice, lemon natural flavor, and allulose. Thereafter, the composition is mixed and processed by heat until the liquid temperature reaches 180° F., bottled into an HDPE bottle at 165° F., and cooled to a temperature of no more than 95° F. rapidly.

TABLE 1

| Ingredient | Units | 1 | 2 | 3 | 4 |
|---|---|---|---|---|---|
| Water | g | 340 | 425 | 330 | 335 |
| R-1,3-BDO | g | 8 | 27 | 17 | 14 |
| D-BHB (as acid) | g | 1 | 3 | 4 | .5 |
| D-BHB (as Mg D-BHB) | g | 1 | 0 | 0 | 2 |
| Lemon juice | g | 2 | 1 | 0.5 | 4 |
| Lemon Natural Flavor | mg | 50 | 100 | 150 | 50 |
| Allulose | g | 10 | 10 | 10 | 10 |

Example 5: Ketogenic Tonic Shot

This example describes a process for preparing a therapeutically effective nutritional composition referred to herein as a ketogenic tonic shot. Combine all of the following ingredients together in a small bottle. Cap, shake to combine, and take like a "shot".

20 g water
15 g lemon juice
13 g R-BDO
3 g D-BHB (as dosed by a 3.91 g blend of 0.92 g Na-D-BHB, 1.03 g K-D-BHB, 0.92 g Mg-D-BHB, 1.04 g Ca-D-BHB)

1 g grated fresh ginger
1 g grated fresh turmeric
pinch fresh cracked black pepper
pinch cayenne pepper Examples 6-7: Ketogenic Endurance Nutritional Goo—"Almond Joy" Flavor Examples 6 and 7 describe a process for preparing a ketogenic endurance nutritional "goo" or "gel" having an "Almond Joy®"-like flavor.

Combine unrefined coconut oil and 100% almond butter, mixed in 1:2 ratio and heated over low heat. In this example, 300 g total are mixed, consisting of 100 g coconut oil and 200 g almond butter. Remove from heat once combined.

In a separate container, 100 g total of R-1,3-BDO, D-BHB acid, and sodium D-BHB are pre-mixed as a 85 weight % BDO (85 g), 10 weight % BHB (as acid) (10 g), and 5 weight % Na-D-BHB (5 g, of which 4.1 g is D-BHB and 0.9 g is Na) solution. This solution is termed the "ketone pre-blend."

While stirring, the ketone pre-blend is slowly added to the coconut almond butter (in a 1:3 ratio).

Blend in 10 g Dutch process cocoa and 20 g allulose.

If stopping here (Example 6), this yields 8 servings of 53.75 g, each containing 12.39 g exogenous ketones.

Optionally, 100 g banana can be added to the overall blend, if a higher carbohydrate load is desired for support of intense physical activity. Blend until smooth. This yields (Example 7), 10 servings of 66.25 g each, each containing 12.39 g exogenous ketones.

Example 8: Kiwi Banana Recovery and Sleep Shake

This example describes a process for preparing a kiwi banana flavored, ketogenic recovery and sleep shake. Blend the following ingredients until smooth:
1.5 c Greek yogurt
½ cup tahini
¾ c frozen banana
2 kiwis, chopped, skin-on
2 TBSP unflavored collagen peptides
2 tsp ground sprouted flax seed
18 g R-1,3-BDO
2.215 g Mg-D-BHB (therein containing 1.8 g D-BHB)
2.2 g D-BHB Acid
Cinnamon to taste
*Stevia* and/or Monkfruit to taste
Serve immediately, within 1 hour after exercise and at least 1 hour before bed.

Example 9: Chocolate Chip Meal Replacement Bar

This example describes a process for preparing a ketogenic nutritional composition. The process makes one chocolate chip-flavored meal replacement bar with 20 g ketones.

Melt 5 g cacao butter. Add 25 g cashew butter, 17 g R-BDO, 1 g D-BHB acid, 1 g vanilla extract, 1 g coconut oil, and stir until combined. Add 15 g soluble tapioca fiber, 15 g whey protein, 10 g almond flour, 5 g allulose, 1 g D-BHB (as dosed by a 1.303 g blend of 0.305 g Na-D-BHB, 0.344 g K-D-BHB, 0.308 g Mg-D-BHB, 0.346 g Ca-D-BHB).

Fold in 1 g chopped roasted walnuts, 1 g chopped roasted cashews, and 4 g sugar free chocolate chips.

Press mixture into a lined tray in a bar shape. Remove when cooled, wrap with parchment paper, and store in the fridge.

Example 10: Blood D-BHB Pharmacokinetics Comparison of Different Nutritional Compositions The blood D-BHB pharmacokinetics produced by different ketogenic nutritional compositions were evaluated and compared. The nutritional compositions include: 100% R-BDO; 90 wt. % R-BDO+10 wt. % D-BHB (acid/salt); 85 wt. % R-BDO+15 wt. % D-BHB (acid/salt); 80 wt. % R-BDO+20 wt. % D-BHB (acid/salt); 75 wt. % R-BDO+25 wt. % D-BHB (acid/salt); 70 wt. % BDO+30 wt. % D-BHB; 60 wt. % BDO+40 wt. % D-BHB; and 50% BDO+50% D-BHB via R-1,3 BDO–D-BHB monoester. The compositions were administered at a dose of 0.5 g (total BDO or BHB excluding mineral or base pairs)/bodyweight kg. Table 2 reports the raw data as shown in FIG. 1. As shown in FIG. 1, ketogenic compositions containing greater than 25 wt. % D-BHB exhibit a rapid spike and crash of D-BHB in the blood. In contrast, the disclosed ketogenic compositions containing high levels of BDO (80 wt. %, 85 wt. % 90 wt. %, respectively) and lower levels of D-BHB provide elevated and sustained ketosis within "optimal therapeutic ketosis" range (between 1 and 2.5 mM D-BHB). This demonstrates the capability of the disclosed compositions to simultaneously account for improved speed of entering "optimal therapeutic ketosis" D-BHB blood concentration, improved duration of time within the "optimal therapeutic ketosis" D-BHB blood concentration, mitigating risk of crossing above the high-end bound of "optimal therapeutic ketosis", and improving palatability and GI distress risk inherent with the prior art ketone and ketogenic precursor compositions.

TABLE 2

| | | | | Blood D-BHB mM pharmacokinetics over time | | | | |
|---|---|---|---|---|---|---|---|---|
| Minutes | 100% R-1,3-BDO (natural) | 90% R-1,3-BDO + 10% D-BHB acid (/D-BHB salt by moles) | 85% R-1,3-BDO + 15% D-BHB acid (/D-BHB salt by moles) | 80% R-1,3-BDO + 20% D-BHB acid (/D-BHB salt by moles) | 75% BDO + 25% D-BHB acid | 70% BDO + 30% D-BHB acid | 60% BDO + 40% D-BHB acid | 50% BDO + 50% D-BHB acid/D-BHB BDO monoester |
| 0 | 0.3 | 0.3 | 0.3 | 0.3 | 0.3 | 0.3 | 0.3 | 0.3 |
| 60 | 1.5 | 2.3 | 2.475 | 2.65 | 2.7 | 2.9 | 3.3 | 4.3 |
| 120 | 1.95 | 2.7 | 2.45 | 2.2 | 2.15 | 2.1 | 2 | 1.9 |
| 180 | 2.15 | 2.18 | 2.09 | 2 | 1.75 | 1.5 | 1.4 | 1.3 |

TABLE 2-continued

Blood D-BHB mM pharmacokinetics over time

| Minutes | 100% R-1,3-BDO (natural) | 90% R-1,3-BDO + 10% D-BHB acid (/D-BHB salt by moles) | 85% R-1,3-BDO + 15% D-BHB acid (/D-BHB salt by moles) | 80% R-1,3-BDO + 20% D-BHB acid (/D-BHB salt by moles) | 75% BDO + 25% D-BHB acid | 70% BDO + 30% D-BHB acid | 60% BDO + 40% D-BHB acid | 50% BDO + 50% D-BHB acid/D-BHB BDO monoester |
|---|---|---|---|---|---|---|---|---|
| 240 | 1.55 | 1.78 | 1.84 | 1.9 | 1.45 | 1 | 0.7 | 0.5 |
| 300 | 1.225 | 1.6 | 1.55 | 1.5 | 1.1 | 0.7 | 0.5 | 0.3 |
| 360 | 0.925 | 1.2 | 1.05 | 0.9 | 0.65 | 0.4 | 0.3 | 0.2 |

Figure 2:
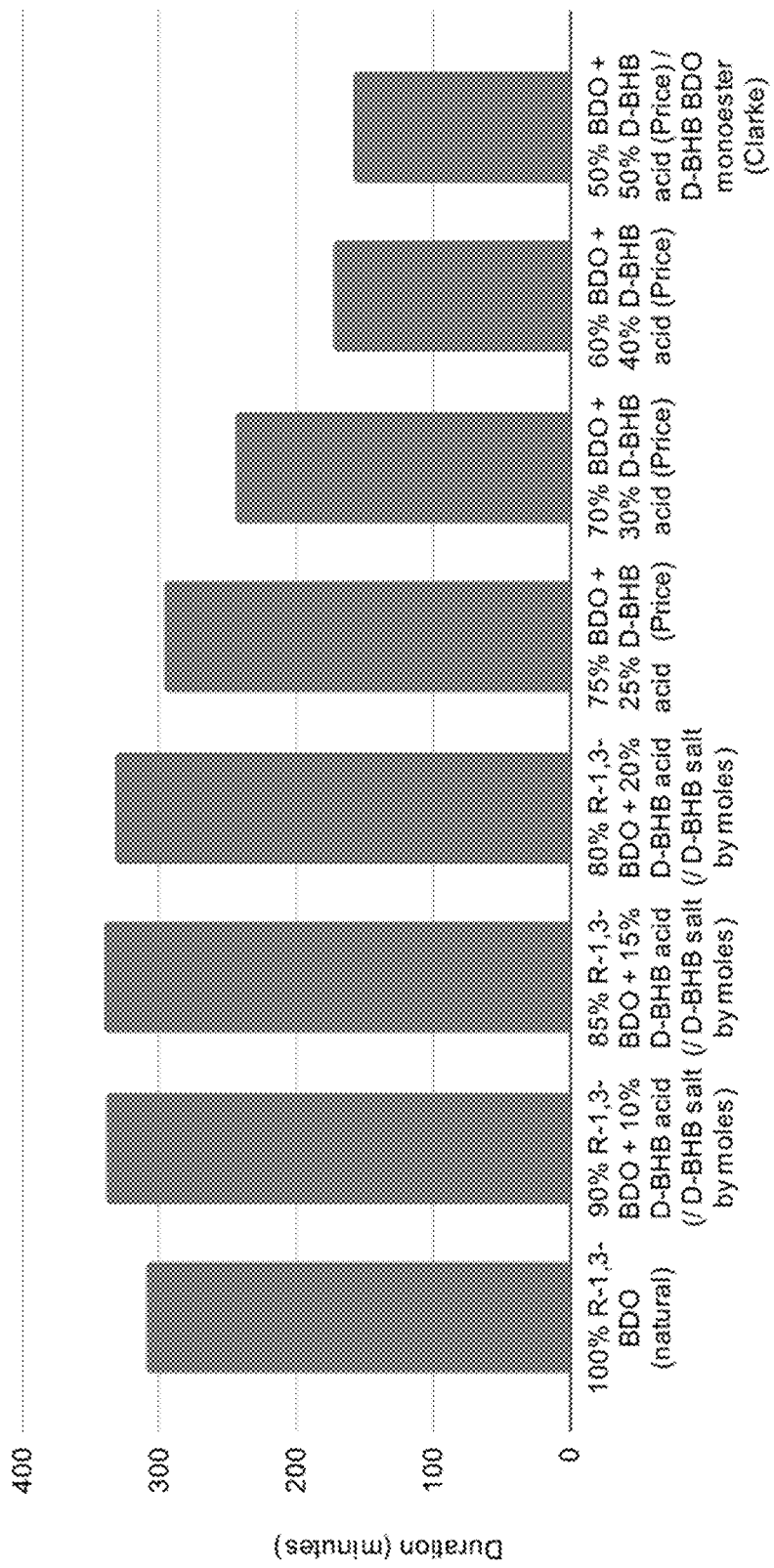
FIG. 2 shows the duration of blood D-BHB concentrations between 1 mM and 2.5 mM for the eight ketogenic compositions reported in FIG. 1.

FIG. 2 shows duration of blood D-BHB concentrations between 1 mM-2.5 mM produced by different ketogenic nutritional compositions. The nutritional compositions include: 100% R-BDO; 90 wt. % R-BDO+10 wt. % D-BHB (acid/salt); 85 wt. % R-BDO+15 wt. % D-BHB (acid/salt); 80 wt. % R-BDO+20 wt. % D-BHB (acid/salt); 75 wt. % R-BDO+25 wt. % D-BHB (acid/salt); 70 wt. % BDO+30 wt. % D-BHB; 60 wt. % BDO+40 wt. % D-BHB; and 50% BDO+50% D-BHB via R-1,3 BDO–D-BHB monoester.

Table 3 reports the raw data as shown in FIG. 2. As shown in FIG. 2, the prior art ketogenic compositions containing greater than 25 wt. % D-BHB have relatively short durations within the "optimal therapeutic ketosis" zone. In contrast, the disclosed ketogenic compositions containing high levels of BDO (80 wt. %, 85 wt. % 90 wt. %, respectively) and lower levels of D-BHB provide elevated and sustained ketosis within the "optimal therapeutic ketosis" range (between 1 and 2.5 mM D-BHB) and delivering upwards of 125% improvement in duration. Prior art compositions focused on achieving ketosis, regardless of peak or duration, via exogenous means, and were less interested in the duration of BHB within an optimal range as key objective functions for their nutritional compositions. This is important from an end user perspective, since prior art compositions require the consumption of multiple doses over time. The disclosed compositions eliminate the need for complex dosing regimens with multiple variable doses over time. This further demonstrates the capability of the disclosed compositions to simultaneously account for improved speed of entering "optimal therapeutic ketosis" D-BHB blood concentration, improved duration of time within the "optimal therapeutic ketosis" D-BHB blood concentration, mitigating risk of crossing above the high-end bound of "optimal therapeutic ketosis", and improving palatability and GI distress risk inherent with the prior art ketone and ketogenic precursor compositions.

Figure 3:
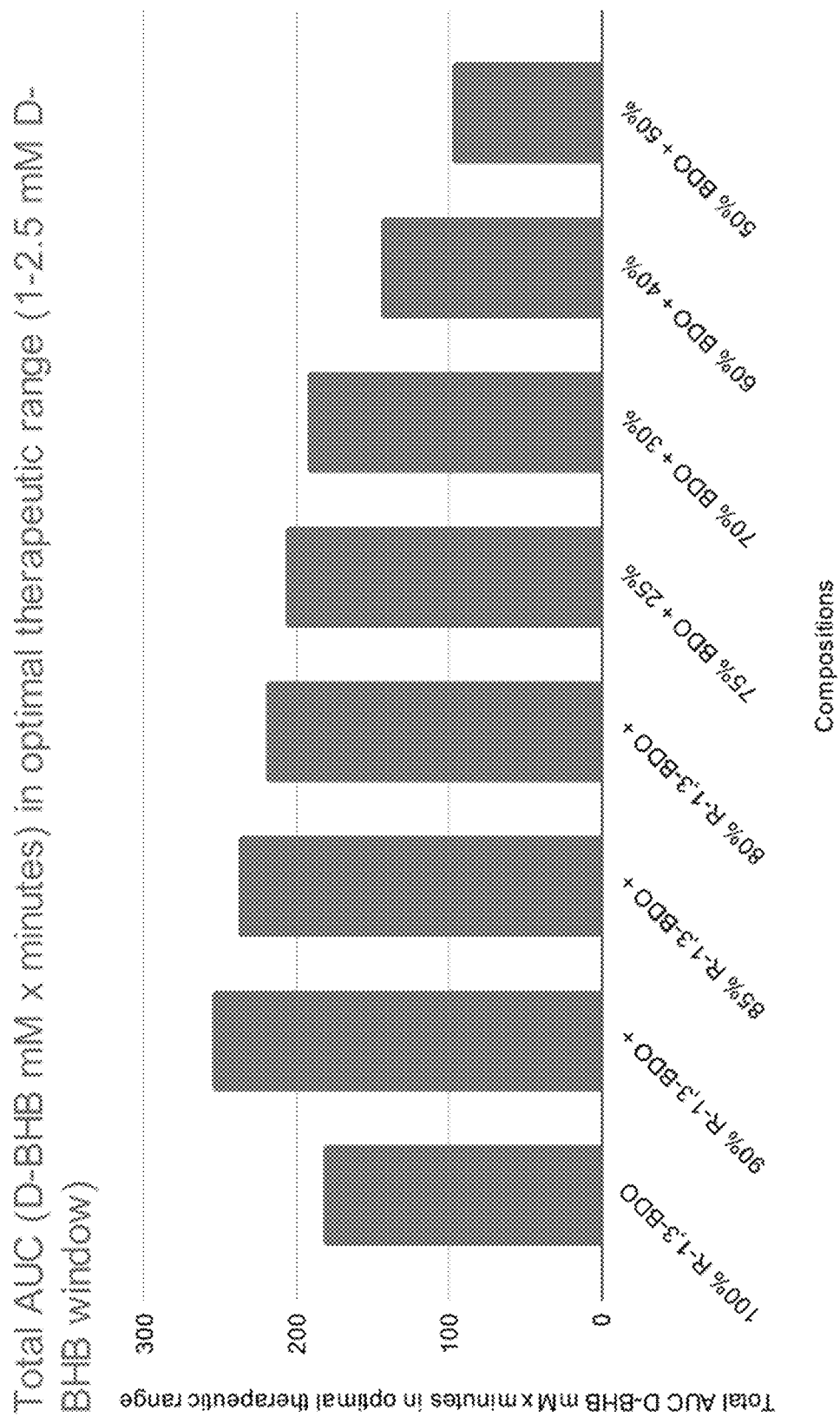
FIG. 3 shows total area under the curve (AUC) mM×minutes in the "optimal therapeutic ketosis" range (1 to 2.5 mM D-BHB) for the eight ketogenic compositions reported in FIG. 1.

FIG. 3 shows the total area under the curve (AUC) mM×minutes in the "optimal therapeutic ketosis" range (1 to 2.5 mM D-BHB). The area under the plot of plasma concentration of a drug versus time after dosage (called "area under the curve" or AUC) gives insight into the extent of exposure to a drug and its clearance rate from the body. By integrating over time rather than looking at individual concentration measurements, a more accurate estimate of the overall exposure to the drug is obtained.

Table 4 reports the raw data as shown in FIG. 3. As shown in FIG. 3, ketogenic compositions containing greater than 25 wt. % D-BHB exhibit relative and monotically lower AUC mM×minutes, whereas in contrast, the disclosed ketogenic compositions containing high levels of BDO (80 wt. %, 85 wt. %, 90 wt. %, respectively) and lower levels of D-BHB provide significantly elevated and sustained ketosis within the "optimal therapeutic ketosis" range. Given new understanding of the physiology of BHB and its signaling impact in the "optimal therapeutic ketosis" range, the AUC of D-BHB blood concentration by time duration within the range, is significant. Prior art compositions focused on achieving ketosis, regardless of peak or duration, via exogenous means, and were less interested in the AUC of BHB within an optimal range. This is important from an end user perspective, since prior art compositions require the consumption of multiple doses over time. The disclosed compositions herein eliminate the need for complex dosing regimens with multiple variable doses over time and further reaffirms the capability of the disclosed compositions to simultaneously account for improved speed of entering "optimal therapeutic ketosis" D-BHB blood concentration, improved duration of time within the "optimal therapeutic ketosis" D-BHB blood concentration, mitigating risk of crossing above the high-end bound of "optimal therapeutic ketosis", and improving palatability and GI distress risk inherent with the prior art ketone and ketogenic precursor compositions.

TABLE 3

Duration of Blood D-BHB Concentrations between 1 mM and 2.5 mM

| | 100% R-1,3-BDO (natural) | 90% R-1,3-BDO + 10% D-BHB acid (/D-BHB salt by moles) | 85% R-1,3-BDO + 15% D-BHB acid (/D-BHB salt by moles) | 80% R-1,3-BDO + 20% D-BHB acid (/D-BHB salt by moles) | 75% BDO + 25% D-BHB acid | 70% BDO + 30% D-BHB acid | 60% BDO + 40% D-BHB acid | 50% BDO + 50% D-BHB acid (Price)/D-BHB BDO monoester |
|---|---|---|---|---|---|---|---|---|
| Duration (minutes) | 310 | 339 | 341 | 332 | 296 | 245 | 173 | 158 |

TABLE 4

| | 100% R-1,3-BDO (natural) | 90% R-1,3-BDO + 10% D-BHB acid (/D-BHB salt by moles) | 85% R-1,3-BDO + 15% D-BHB acid (/D-BHB salt by moles) | 80% R-1,3-BDO + 20% D-BHB acid (/D-BHB salt by moles) | 75% BDO + 25% D-BHB acid | 70% BDO + 30% D-BHB acid | 60% BDO + 40% D-BHB acid | 50% BDO + 50% D-BHB acid (Price)/D-BHB BDO monoester |
|---|---|---|---|---|---|---|---|---|
| Total AUC mM × minutes in "optimal therapeutic ketosis" range of 1-2.5 mM | | | | | | | | |
| Total AUC mM × minutes in optimal therapeutic range | 183 | 256 | 238 | 221 | 207 | 193 | 146 | 98.3 |

Example 11: System for Personalizing D-Beta-Hydroxybutyrate and R-1,3-Butanediol Nutritional Compositions This example describes a novel system to personalize a D-beta-hydroxybutyrate and R-1,3-butanediol based nutritional composition and/or beverage to deliver the optimal pharmacokinetics of D-beta-hydroxybutyrate for a specific individual human's idiosyncratic metabolism of ketones and adaptation to ketosis.

The disclosed system has two stages:

Stage 1: the measurement of the idiosyncratic rate of ketone metabolism of an individual subject, and Stage 2: determining the optimal ratio of R-1,3 butanediol (BDO) to D-BHB free acid or D-BHB ketone salt in a nutritional composition or beverage medium.

R-1,3-butanediol converts into D-BHB through the liver in a non-classical hepatic ketogenic pathway. This speed of conversion is rate-limited and idiosyncratic to the individual.

On the other hand, D-BHB free acid or D-BHB salt, which rapidly dissociates into D-BHB free acid and its mineral counterpart in a water solution, directly delivers D-BHB into the stomach and small intestine, and D-BHB is rapidly uptaken in the individual subject's gastrointestinal system.

Thus, one can describe BDO as a "slow-release" ketone precursor molecule and D-BHB as an "immediate/fast release" ketone molecule.

A person's individual metabolism and adaptation to ketosis is affected by genetic and environmental factors, including but not limited to genetics, basal metabolic rate, the person's adaptation to aerobic or anaerobic exercise, the person's adaptation to a low-carb, high-fat diet or a mixed, Standard American Diet.

There is significant prior art specifying specific molecules of exogenous ketone or ketone precursors. However, these all fail to account for the personal idiosyncrasies of individual human's genetics, behavior, and environment which impact the metabolism of such nutritional compositions for its intended effects.

The disclosed two-stage system accounts for idiosyncratic metabolism of each individual, determines it, and then produces a nutritional composition and/or beverage optimized for the individual.

Stage 1: Determine the Idiosyncratic Rate of Ketone Metabolism of the Individual Over the course of 1 day or 2 separate days, the subject drinks a 25 g (range between 1-100 g) D-BHB acid/salt beverage and measures and tracks blood D-BHB levels every 30 minutes for 3 hours. Time ranges can include every 1 minute to every 1 hour, from 1 hour to 10 hours.

After at least 3 hours after the end of the first drink on the same day or after a separate day, the subject drinks a 25 g (range of 1-100 g) BDO beverage and, using a blood D-BHB measurement device, measures and tracks blood D-BHB levels every 30 minutes for 3 hours.

These two pharmacokinetic datapoints are stored as two series of tuples (timestamp, blood BHB) labeled as tuple "fast-ketone" and tuple "slow-ketone".

These two series then generate 100 different series by averaging together the tuples with 99 different weights for the tuple series, ranging from 1:99 (representing 1%-99% D-BHB) and 99:1 (representing 99%-1%) of BDO. These tuples are labeled as "1-fast, 99-slow", "2-fast, 98-slow", . . . 99-fast, 1-slow".

Optionally, we can add a tuning step of the process by optimizing for a specific individual's desired use case by setting a floor BHB level. For athletic performance, the floor BHB level is 2.0. For cognitive or general daily use, the floor BHB level is 0.5. In the generated tuples, for values below the "floor BHB level", the blood BHB coordinate is set to 0.

These 99 tuple series are each summed individually. The highest sum of blood BHB across the 99 in the "x-fast, y-slow" tuple series, predicts the personalized optimal ratios of D-BHB acid/salt and BDO, as x % D-BHB and y % BDO, where x+y=100%.

All publications, patents, patent applications, or other documents cited herein are hereby incorporated by reference in their entirety for all purposes to the same extent as if each individual publication, patent, patent application, or other document was individually indicated to be incorporated by reference for all purposes.

While this disclosure has been particularly shown and described with references to preferred embodiments thereof, it will be understood by those skilled in the art that various changes in form and details may be made therein without departing from the scope of the disclosure encompassed by the appended claims.

What is claimed is:

1. A nutritional composition comprising a mixture of ketogenic ingredients, wherein the ketogenic ingredients consist essentially of:
   80 to 95% w/w of 1,3-butanediol (BDO) selected from R-1,3-butanediol, S-1,3-butanediol, and racemic 1,3-butanediol; and
   5 to 20% w/w of beta-hydroxybutyric acid (BHB) selected from D-beta-hydroxybutyric (D-BHB) acid, L-beta-hydroxybutyric (L-BHB) acid, racemic beta-hydroxybutyric acid and/or an equivalent molar amount of its conjugate base D-beta-hydroxybutyrate, L-beta-hydroxybutyrate, racemic beta-hydroxybutyrate or a salt, monoester, polyester, or mixture thereof.

2. The nutritional composition of claim 1, wherein the BDO is from 85 to 95% w/w and the BHB is from 5 to 15% w/w.

3. The nutritional composition of claim 1, wherein the BDO is from 85 to 92% w/w and the BHB is from 8 to 15% w/w.

4. The nutritional composition of claim 1, wherein the BDO is from 87 to 90% w/w and the BHB is from 10 to 13% w/w.

5. The nutritional composition of claim 1, wherein the BDO comprises R-1,3-butanediol.

6. The nutritional composition of claim 1, wherein the ketogenic ingredients are present in the composition in an amount ranging from 1 gram to 100 grams.

7. The nutritional composition of claim 1, wherein the ketogenic ingredients are present in the composition in an amount ranging from 10 grams to 30 grams.

8. The nutritional composition of claim 7, wherein the BDO is from 85 to 95% w/w and the BHB is from 5 to 15% w/w.

9. The nutritional composition of claim 7, wherein the BDO is from 87 to 90% w/w and the BHB is from 10 to 13% w/w.

10. The nutritional composition of claim 1, wherein said composition is prepared in a beverage form, a powder form, a softgel form, a goo form, a bar form, a bite form, or a capsule form.

11. A nutritional beverage or food product configured to produce in a subject a blood concentration of D-BHB of at least approximately 2.0 mM at 180 minutes post consumption of the nutritional beverage or food product, the nutritional beverage or food product comprising a nutritional composition of ketogenic ingredients, and one or more of a consumable carrier, an excipient, a flavoring agent, and a sweetener, wherein the ketogenic ingredients consist essentially of a first ketogenic ingredient selected from the group consisting of 1,3-butanediol (BDO), R-1,3-butanediol, S-1,3-butanediol, or racemic 1,3-butanediol in an amount of 80 to 95% w/w, and a second ketogenic ingredient selected from the group consisting of beta-hydroxybutyric acid (BHB), D-beta-hydroxybutyric (D-BHB) acid, L-beta-hydroxybutyric (L-BHB) acid, and racemic beta-hydroxybutyric acid, and/or an equivalent molar amount of its conjugate base D-beta-hydroxybutyrate, L-beta-hydroxybutyrate, racemic beta-hydroxybutyrate or a salt, monoester, polyester, or mixture thereof, in an amount of 5 to 20% w/w.

12. The nutritional beverage or food product of claim 11, wherein the ketogenic ingredients are present in the nutritional beverage or food product in an amount ranging from 1 gram to 100 grams,
    wherein the sweetener is selected from *stevia*, steviol glycosides, allulose, monk fruit, mogrosides, or a combination thereof.

13. The nutritional beverage or food product of claim 11, wherein the ketogenic ingredients are present in the nutritional beverage or food product in an amount ranging from 10 grams to 30 grams,
    wherein the sweetener is selected from *stevia*, steviol glycosides, allulose, monk fruit, mogrosides, or a combination thereof.

14. A method of producing optimal therapeutic ketosis in a subject, the method comprising administering to the subject a nutritional composition, the nutritional composition comprising a mixture of ketogenic ingredients consisting essentially of 80 to 95% w/w of 1,3-butanediol (BDO) selected from R-1,3-butanediol, S-1,3-butanediol, racemic 1,3-butanediol, and 5 to 20% w/w beta-hydroxybutyric acid (BHB), selected from D-beta-hydroxybutyric (D-BHB) acid, L-beta-hydroxybutyric (L-BHB) acid, and racemic beta-hydroxybutyric acid, and/or an equivalent molar amount of its conjugate base D-beta-hydroxybutyrate, L-beta-hydroxybutyrate, racemic beta-hydroxybutyrate or a salt, monoester, polyester, or mixture thereof,
    wherein a blood concentration of D-BHB in the subject is at least approximately 2.0 mM at 180 minutes post consumption of the nutritional composition.

15. The method of claim 14, wherein the ketogenic ingredients are present in the nutritional composition in an amount ranging from 1 grams to 100 grams.

16. The method of claim 14, wherein the ketogenic ingredients are present in the nutritional composition in an amount ranging from 10 grams to 30 grams.

* * * * *